US012758344B2

(12) United States Patent
Azar et al.

(10) Patent No.: US 12,758,344 B2
(45) Date of Patent: Oct. 13, 2026

(54) MINIMALLY INVASIVE SURGICAL INSTRUMENT SUPPORT STAND

(71) Applicant: MeaCor, Inc., Ayer, MA (US)

(72) Inventors: Toufic Azar, Boston, MA (US); Omar Labban, Beirut (LB); Anthony Eid, Baabda (LB); Renzo Cecere, Montreal (CA)

(73) Assignee: MEACOR, INC., Irvine, CA (US)

( * ) Notice: Subject to any disclaimer, the term of this patent is extended or adjusted under 35 U.S.C. 154(b) by 102 days.

(21) Appl. No.: 18/675,755

(22) Filed: May 28, 2024

(65) Prior Publication Data

US 2025/0120783 A1 Apr. 17, 2025

Related U.S. Application Data

(63) Continuation of application No. PCT/IB2022/061662, filed on Dec. 1, 2022.

(60) Provisional application No. 63/284,949, filed on Dec. 1, 2021.

(51) Int. Cl.
*A61B 50/24* (2016.01)

(52) U.S. Cl.
CPC .................................... *A61B 50/24* (2016.02)

(58) Field of Classification Search
CPC . A61B 90/50; A61B 90/57; A61B 2090/5025; A61B 2090/504; A61B 2090/506; A61B 2090/571; A61B 50/26; A61B 50/28; A61B 1/00149; A61B 8/4405; B25J 9/106; B25J 9/1065
See application file for complete search history.

(56) References Cited

U.S. PATENT DOCUMENTS 5,098,048 A 3/1992 Chen
5,358,204 A * 10/1994 Terada ..................... G10H 1/32 108/118
5,575,793 A 11/1996 Carls et al.
6,309,397 B1 10/2001 Julian et al.
(Continued)

FOREIGN PATENT DOCUMENTS

CN 107720648 A 2/2018
CN 111268590 A * 6/2020 ............. A61B 90/50
(Continued)

OTHER PUBLICATIONS

PCT/IB2022/061662 International Preliminary Report on Patentability dated Jun. 13, 2024.
(Continued)

*Primary Examiner* — Martin T Ton
(74) *Attorney, Agent, or Firm* — William A. English; Vista IP Law Group LLP

(57) ABSTRACT

A support stand (10) for a minimally invasive surgical instrument (12), comprising first and second scissored arms (22 and 24) intersecting each other at an arm pivot (54); and an instrument holder (20) for holding the minimally invasive surgical instrument (12), the instrument holder (20) being supported by the first and second arms (22 and 24); wherein the first and second arms (22 and 24) are selectively pivotable relative to each other about the arm pivot (54) and wherein the arm pivot (54) is selectively movable along the first and second arms (22 and 24).

53 Claims, 9 Drawing Sheets

(56) References Cited

U.S. PATENT DOCUMENTS

| | | | | |
|---|---|---|---|---|
| 6,857,493 | B2 * | 2/2005 | Shupp | B66F 7/14 318/587 |
| 8,409,273 | B2 | 4/2013 | Thornton et al. | |
| 8,974,408 | B2 | 3/2015 | Wallace et al. | |
| 9,119,716 | B2 | 9/2015 | Lee et al. | |
| 9,211,160 | B2 | 12/2015 | Pivotto et al. | |
| 9,724,192 | B2 | 8/2017 | Sheps et al. | |
| 10,799,312 | B2 | 10/2020 | Tyler, II et al. | |
| 11,047,520 | B1 * | 6/2021 | Schwind | A47B 97/08 |
| 11,931,525 | B2 | 3/2024 | Jamal et al. | |
| 12,251,176 | B2 | 3/2025 | Moll et al. | |
| 2011/0130718 | A1 * | 6/2011 | Kidd | A61B 34/30 604/95.01 |
| 2015/0190201 | A1 | 7/2015 | Olson | |
| 2015/0327939 | A1 | 11/2015 | Kokish et al. | |
| 2015/0328068 | A1 * | 11/2015 | Hruschka | A61G 7/018 254/122 |
| 2019/0053863 | A1 | 2/2019 | Hongo et al. | |
| 2019/0247128 | A1 | 8/2019 | Inouye et al. | |
| 2020/0108225 | A1 | 4/2020 | Jamal et al. | |
| 2020/0238542 | A1 | 7/2020 | Castro et al. | |
| 2023/0201536 | A1 | 6/2023 | Bowes et al. | |
| 2023/0346499 | A1 * | 11/2023 | Zhang | A61M 25/0113 |

FOREIGN PATENT DOCUMENTS

| | | | |
|---|---|---|---|
| GB | 875481 | A | 8/1961 |
| WO | WO-2023100135 | A1 | 6/2023 |

OTHER PUBLICATIONS

PCT/IB2022/061662 International Search Report and Written Opinion dated Feb. 24, 2023.

European Patent Office, Extended European Search Report for corresponding European Application No. 22900783.6-1113, Oct. 14, 2025, 19 pages.

* cited by examiner

FIG. 1
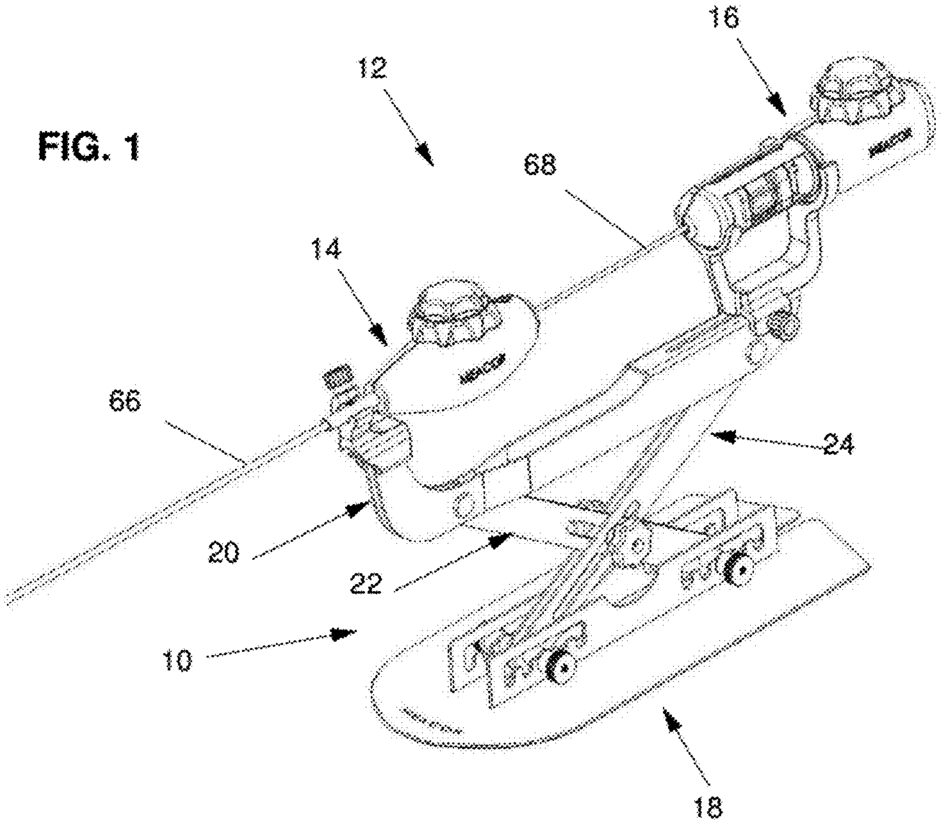
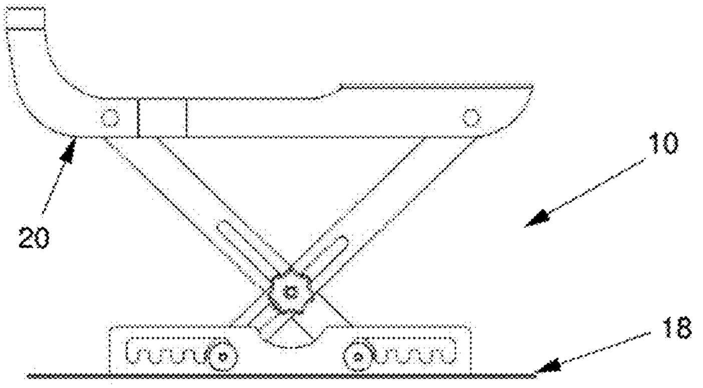
FIG. 3A
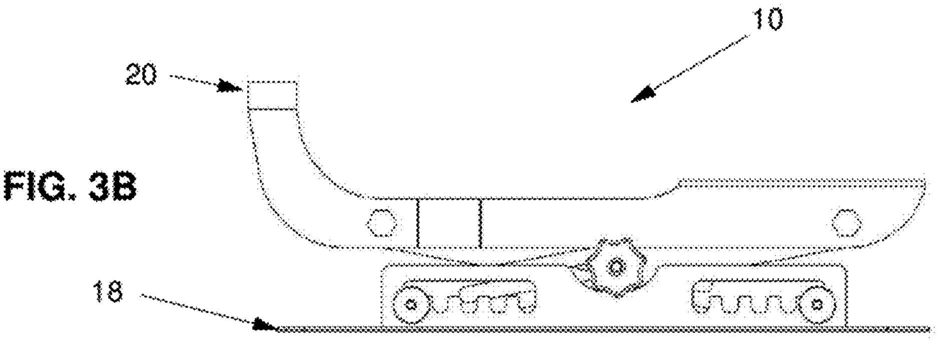
FIG. 3B

FIG. 2
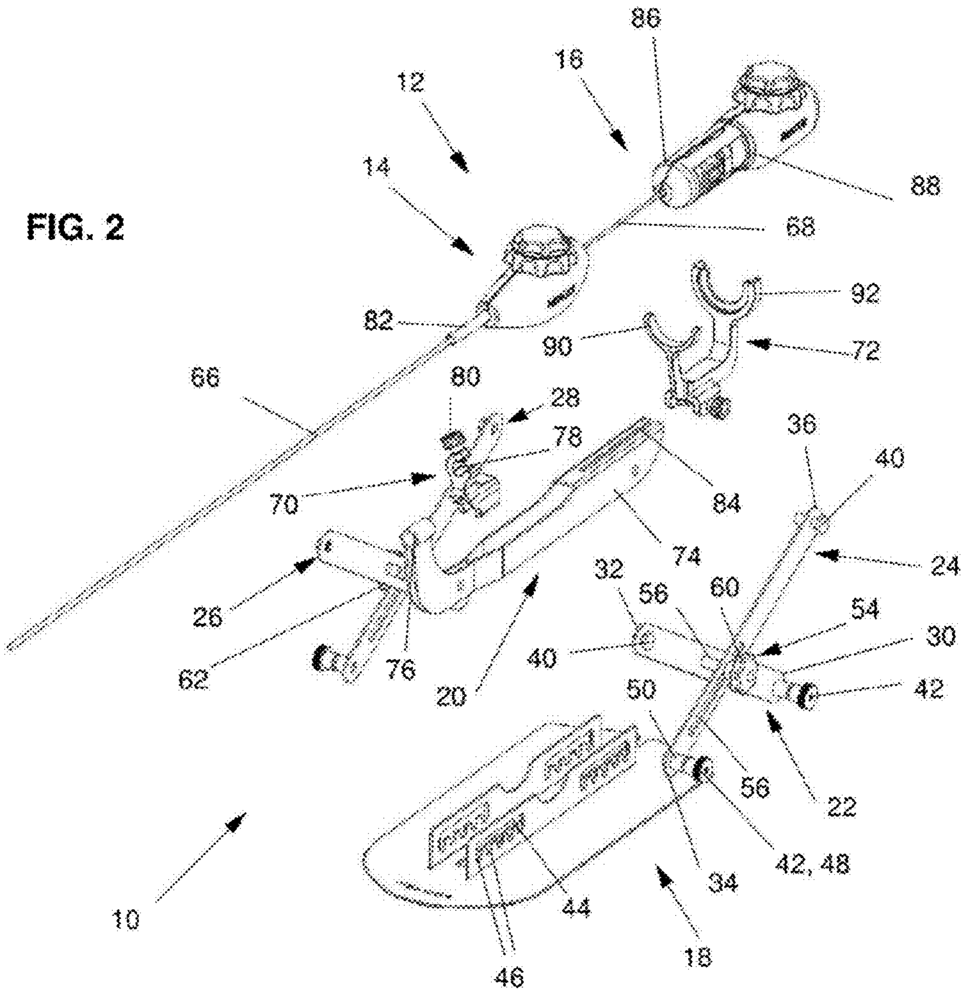
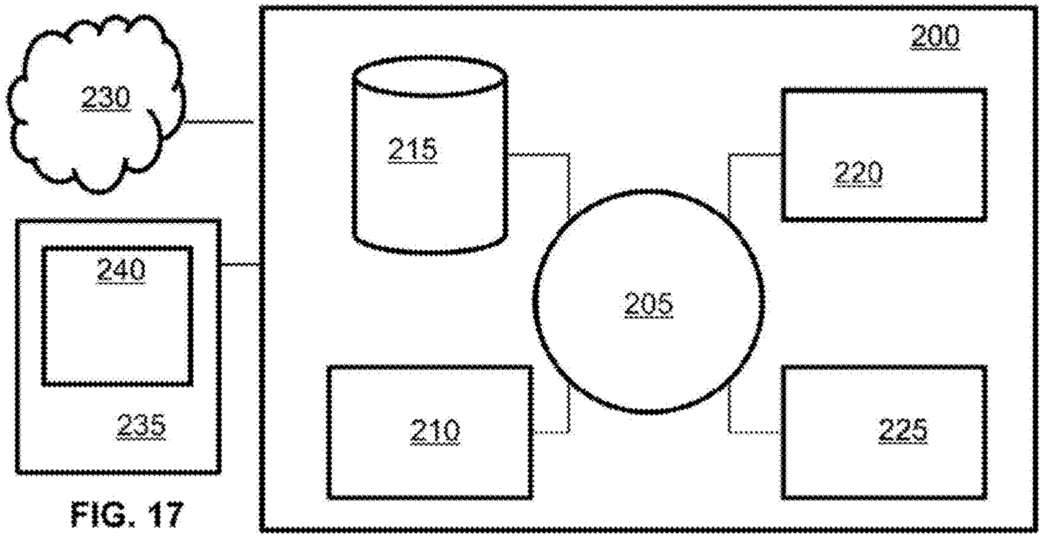
FIG. 17

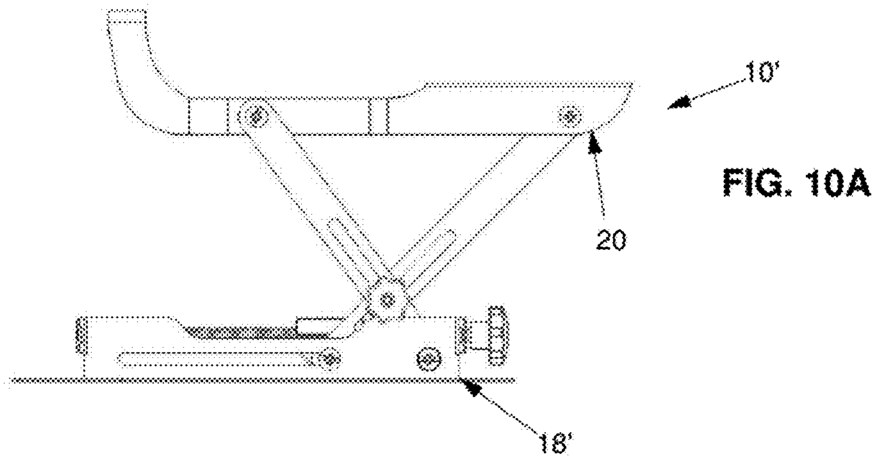
FIG. 10A
FIG. 10B
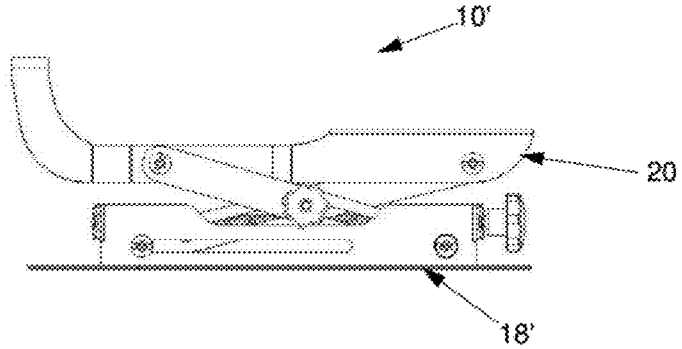
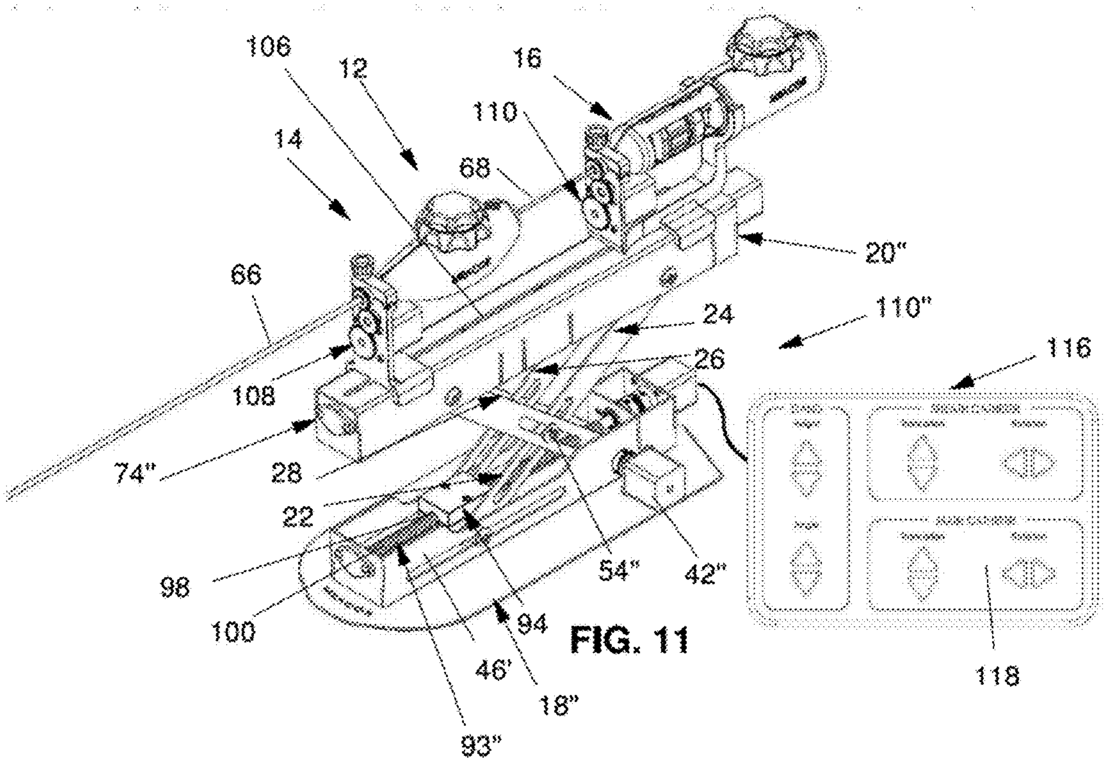
FIG. 11

MINIMALLY INVASIVE SURGICAL INSTRUMENT SUPPORT STAND

CROSS-REFERENCE

This application is a continuation of International Patent Application No. PCT/IB2022/061662, filed Dec. 1, 2022, which claims the benefit of U.S. Provisional Patent Application No. 63/284,949, filed Dec. 1, 2021, each of which is entirely incorporated herein by reference.

FIELD OF THE INVENTION

The present invention relates to the general field of surgery, and is more particularly concerned with a minimally invasive surgical instrument support stand.

BACKGROUND

Catheter devices are inserted through a catheter, which is itself inserted through the vasculature of a patient to perform many procedures without requiring major surgery to access an intervention site. The angle and position of the catheter relative to the patient need to be precisely controlled to optimize these procedures. The catheter devices and/or the catheter themselves are therefore often supported by a stand to maintain this relative position and angle throughout the procedure. Some of these stands are adjustable to adjust these parameters prior to starting the procedure, or during the procedure if needed. Current stands have limited adjustability, and are therefore not optimal, especially when patients having very different morphologies are to be treated using the same stand, or when the stand is used to perform animal studies or treatments.

Accordingly, there exists a need for improved support stands. An object of the invention is to provide such support stands.

SUMMARY OF THE INVENTION

In a broad aspect, there is provided a catheter device support stand, comprising: a base; a holder assembly spaced apart from the base and configured for holding the catheter device; and first and second arms extending between the base and the holder assembly, the first arm defining a first arm base end and an opposed first arm holder end, the second arm defining a second arm base end and an opposed second arm holder end. The holder assembly and the first and second arms are pivotally mounted to each other at the first and second arm holder ends with the first and second arm holder ends spaced apart from each other. The base and the first and second arms are pivotally mounted to each other at the first and second arm base ends with the first and second arm base ends spaced apart from each other. The first and second arms are pivotally secured to each other through a pivot between the first and second arm holder and base ends, the pivot being selectively movable along the first and second arms. At least one of the first and second arms base or holder end is selectively movable relative to respectively the base or holder assembly to allow variations in a distance between respectively the first and second arm base or holder ends.

In a broad aspect, there is provide a support stand for a minimally invasive surgical instrument, comprising: first and second scissored arms intersecting each other at an arm pivot; and an instrument holder for holding the minimally invasive surgical instrument, the instrument holder being supported by the first and second arms; wherein the first and second arms are selectively pivotable relative to each other about the arm pivot and wherein the arm pivot is selectively movable along the first and second arms.

There may also be provided a support stand further comprising a base, the first and second arms extending between the instrument holder and the base, wherein pivoting the first and second arms relative to each other and moving the arm pivot along the first and second arms allows varying a distance and a relative orientation between the base and the instrument holder.

There may also be provided a support stand wherein each of the first and second arms defines opposed arm base and holder ends respectively at the base and at the instrument holder; and the arm base end of at least one of the first and second arms is selectively movable along the base.

There may also be provided a support stand wherein the first and second arms are pivotally mounted to the instrument holder at holder pivots fixed in translation along the instrument holder.

There may also be provided a support stand wherein the arm base end of both the first and second arms are selectively movable along the base.

There may also be provided a support stand wherein the base defines longitudinally spaced apart arm receiving portions for fixedly receiving the first and second arms at discrete longitudinal positions along the base.

There may also be provided a support stand further comprising a translation actuator for selectively moving the arm base end of the at least one of the first and second arms along the base.

There may also be provided a support stand further comprising a lead screw extending along the base and a carriage movable along the lead screw through rotation of the lead screw, the at least one of the first and second arms being mounted to the carriage and pivotable relative thereto.

There may also be provided a support stand wherein an other one of the first and second arms different from the at least one of the first and second arms is fixed along the base and pivotally mounted thereto.

There may also be provided a support stand further comprising a rotation actuator for selectively pivoting the other one of the first and second arms about the base.

There may also be provided a support stand wherein the first and second arms are freely pivotable about the arm pivot and the arm pivot is freely movable along predetermined portions the first and second arms.

There may also be provided a support stand wherein the first and second arms each define a longitudinally extending slot, the arm pivot being received in and guided by the slots.

There may also be provided a support stand wherein the arm pivot is configurable between a locked configuration, a rotatable configuration and a free moving configuration, wherein in the locked configuration, the first and second arms are pivotally fixed relative to each other and the pivot is fixed along the first and second arms; in the rotatable configuration, the first and second arms are pivotable relative to each other and the pivot is fixed along the first and second arms; in the free moving configuration, the first and second arms are pivotable relative to each other and the pivot is movable along the first and second arms.

There may also be provided a support stand wherein the arm pivot includes a knob selectively turnable to vary frictional forces between the first and second arms to move the arm pivot between the locked, rotatable and free moving configurations.

There may also be provided a support stand wherein the minimally invasive surgical instrument includes first and second components, the instrument holder being configured for supporting the first and second components so that a distance between the first and second components is selectively adjustable.

There may also be provided a support stand wherein the surgical instrument holder includes a holder base and a platform for supporting one of the first and second components, the platform being longitudinally movable along the holder base.

There may also be provided a support stand further comprising a platform actuator for selectively moving the platform along the holder base.

There may also be provided a support stand wherein the surgical instrument includes a catheter, the instrument holder holding the surgical instrument so that the surgical instrument is selectively rotatable about a rotation axis colinear with the catheter.

There may also be provided a support stand further comprising a rotation actuator for selectively rotating the surgical instrument about the rotation axis.

In yet another broad aspect, there is provided a support stand for a minimally invasive surgical instrument, comprising: a base; first and second arms intersecting each other and mounted to the base; an arm pivot linking the first and second arms to each other such that the first and second arms are selectively pivotable relative to each other about the arm pivot and the arm pivot is selectively movable along the first and second arms; and an instrument holder for holding the minimally invasive surgical instrument, the instrument holder being supported above the base by the first and second arms; wherein at least one of the first and second arms is movable along at least one of the base and instrument holder; whereby a height and attitude of the instrument holder relative to the base is changed by moving the at least one of the first and second arms along the at least one of the base and instrument holder while allowing either the first and second arm to pivot about the arm pivot with the arm pivot remaining translationally fixed along the first and second arms; or the first and second arm to pivot about the arm pivot and the arm pivot to translate along the first and second arms.

There may also be provided a support stand wherein each of the first and second arms defines opposed arm base and holder ends respectively at the base and at the instrument holder; and the arm base end of at least one of the first and second arms is selectively movable along the base.

There may also be provided a support stand wherein the first and second arms are pivotally mounted to the instrument holder at holder pivots fixed in translation along the instrument holder.

There may also be provided a support stand wherein the arm base end of both the first and second arms are selectively movable along the base.

There may also be provided a support stand wherein the base defines longitudinally spaced notches for fixedly receiving the first and second arms at discrete longitudinal positions along the base.

There may also be provided a support stand further comprising a translation actuator for selectively moving the arm base end of the at least one of the first and second arms along the base.

There may also be provided a support stand wherein the translation actuator includes a lead screw extending along the base and a carriage movable along the lead screw through rotation of the lead screw, the at least one of the first and second arms being mounted to the carriage and pivotable relative thereto in a plane of the first and second arms.

There may also be provided a support stand wherein an other one of the first and second arms different from the at least one of the first and second arms is fixed along the base and pivotally mounted thereto.

There may also be provided a support stand further comprising a rotation actuator for selectively pivoting the other one of the first and second arms about the base in a plane of the first and second arms.

There may also be provided a support stand wherein the first and second arms are freely pivotable about the arm pivot and the arm pivot is freely movable along predetermined portions the first and second arms.

There may also be provided a support stand wherein the first and second arms each define a longitudinally extending slot at a location between the arm base and holder ends, the arm pivot being received in and guided by the slots.

There may also be provided a support stand wherein the arm pivot is configurable between a locked configuration, a rotatable configuration and a free moving configuration, wherein in the locked configuration, the first and second arms are pivotally fixed relative to each other and the pivot is fixed along the first and second arms; in the rotatable configuration, the first and second arms are pivotable relative to each other and the pivot is fixed along the first and second arms; in the free moving configuration, the first and second arms are pivotable relative to each other and the pivot is movable along the first and second arms.

There may also be provided a support stand wherein the arm pivot includes a knob usable to vary a compression force between the first and second arms so as to vary frictional forces between the first and second arms to move the arm pivot between the locked, rotatable and free moving configurations.

There may also be provided a support stand wherein the minimally invasive surgical instrument includes first and second components, the instrument holder being configured for supporting the first and second components so that a distance between the first and second components is selectively adjustable.

There may also be provided a support stand wherein the surgical instrument holder includes a holder base and a platform for supporting one of the first and second components, the platform being longitudinally movable along the holder base.

There may also be provided a support stand further comprising a platform actuator for selectively moving the platform along the holder base.

There may also be provided a support stand wherein the instrument holder is configured so that at least part of the surgical instrument is rotatable about a rotation axis parallel to the instrument holder.

There may also be provided a support stand further comprising a rotation actuator for selectively rotating the at least part of the surgical instrument about the rotation axis.

There may also be provided a support stand further comprising a controller for selectively energizing the actuator.

Advantageously, the proposed device can relatively easily be configured over a large range of distances and angles between the base and holder assembly. This is useful to treat human patients with catheter devices for human patients having very different morphologies as this allows to easily adjust the angle at which a catheter enters the human body. This versatility is also useful in animal studies as the same stand may be used for very different animals. The present PCT application claims priority to U.S. Provisional Application No. 63/284,949, filed Dec. 1, 2021, the contents of which are incorporated herein by reference.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the drawings:

FIG. 1, in a perspective view, illustrates a catheter device support stand in accordance with an embodiment of the present invention;

FIG. 2, in a perspective exploded view, illustrates the catheter device support stand shown in FIG. 1;

FIG. 3A, in a side elevation view, illustrates the catheter device support stand shown in FIG. 1 with a holder assembly thereof in an uppermost position;

FIG. 3B, in a side elevation view, illustrates the catheter device support stand shown in FIG. 1 with the holder assembly in a lowermost position;

FIG. 10A, in a side elevation view, illustrates the catheter device support stand shown in FIG. 7 with a holder assembly thereof in an uppermost position;

FIG. 10B, in a side elevation view, illustrates the catheter device support stand shown in FIG. 7 with the holder assembly in a lowermost position;

FIG. 17, in a schematic view, illustrates a computer system usable to control the catheter device support stand shown in FIG. 11.

DETAILED DESCRIPTION

Figure 4A:
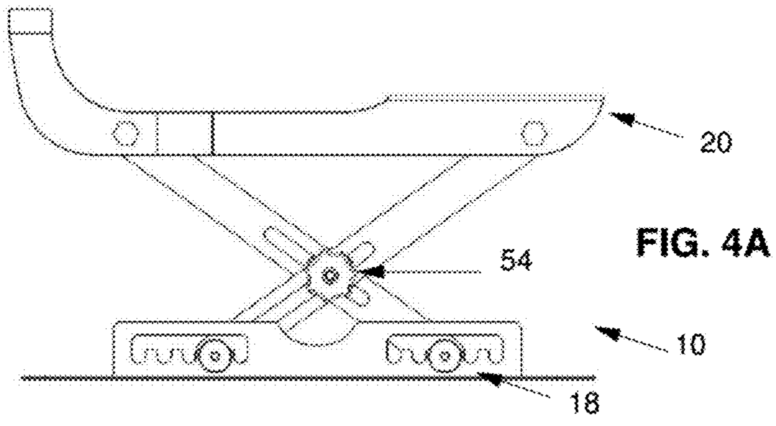
FIG. 4A, in a side elevation view, illustrates the catheter device support stand shown in FIG. 1 with the holder assembly in a level position.

With reference to FIG. 1, there is shown a catheter device support stand 10 for supporting a catheter device 12 or any other suitable minimally invasive surgical instrument. The catheter device 12 includes first and second components 14 and 16 in the embodiment illustrated in FIG. 1, but catheter devices 12 having only one of more than two components are usable in similar catheter device support stands.

The catheter device support stand 10 includes a base 18, a holder assembly 20, which may also be referred to as an instrument holder, spaced apart from the base 18 and configured for holding the catheter device 12 and first and second arms 22 and 24 extending between the base 18 and the holder assembly 20. The first and second arms 22 and 24 are intersecting and are mounted to each other, for example by being scissored to each other, and to the base 18 and holder assembly 20 to allow an intended user to selectively vary a distance and an angle between the base 18 and the holder assembly 20 to provide two degrees of freedom allowing a versatile adjustment of the relative position and orientation of the base 18 and holder assembly 20 relative to each other in a predetermined plane.

In some embodiments, as better seen in FIG. 2, the catheter device support stand 10 also includes third and fourth arms 26 and 28 respectively substantially parallel to and in register with the first and second arms 22 and 24. The third and fourth arms 26 and 28 and mounted to the base 18 and holder assembly 20 similarly respectively to the first and second arms 22 and 24. The first and third arms 22 and 26 are between the second and fourth arms 24 and 28. In some embodiments, the third and fourth arms 26 and 28 are omitted. However, when present, the third and fourth arms 26 and 28 rigidify and increase stability of the catheter device support stand 10 when compared to versions in which only two arms are present without requiring relatively thick first and second arms 22 and 24.

The first arm 22 defines a first arm base end 30 and an opposed first arm holder end 32. The second arm 24 defines a second arm base end 34 and an opposed second arm holder end 36. The holder assembly 20 and the first and second arms 22 and 24 are pivotally mounted to each other at the first and second arm holder ends 32 and 36 with the first and second arm holder ends spaced 32 and 36 apart from each other along the holder assembly, for example through holder pivots 40 that are fixed relative to the holder assembly 20. The third and fourth arms 26 and 28 are similarly mounted to the holder assembly 20.

The base 18 and the first and second arms 22 and 24 are pivotally mounted to each other at the first and second arm base ends 30 and 34 with the first and second arm base ends 30 and 34 spaced apart from each other, for example through base pivots 42. In opposition to the holder pivots 40, at least one, and in some embodiments both, of the base pivots 42 is movable along the base 18. In the embodiment shown in FIG. 2, the base pivots 42 can each be selectively moved within a respective base slot 44 extending along the base 18, for example in a plate part thereof. The base slots 44 each define spaced apart generally downwardly extending notches 46 in which the base pivots 42 are selectively insertable. The notches 46 are typically configured and sized so that a base pivot 42 inserted thereinto is not movable longitudinally along the base slot 44 and thus define longitudinally spaced apart arm receiving portions for fixedly receiving the first and second arms 22 and 24 at discrete longitudinal positions along the base 18. In some embodiments, the base pivots 42 are further lockable in the notches 46. For example, the base pivots 42 may include a knob 48 than can be selectively unscrewed and screwed relative to a spacer 50 mounted at the first and second arms base ends 30 and 34. When the knob 48 is screwed tightly enough, the base 18 may be sandwiched tightly between the knob 48 and spacer 50. The spacer 50 is typically sized so that lateral movements relative to the base slots 44 are prevented. The third and fourth arms 26 and 28 are mounted to the base 18 similarly to the first and second arms 22 and 24. In some embodiments, the notches 46 are omitted and the base pivots 42 are lockable at any location along the base slots 44.

The first and second arms 22 and 24, and when present the third and fourth arms 26 and 28 are pivotally secured to each other through an arm pivot 54 inserted through an arm slot 56 extending along each of the first, second, third and fourth arms 22, 24, 26 and 28. The arm pivot 54 is selectively movable along the first, second, third and fourth arms 22, 24, 26 and 28 by moving the arm pivot 54 along the arm slot 56, so that the arm pivot 54 is freely movable along predetermined portions of the first, second, third and fourth arms 22, 24, 26 and 28. The arm pivot 54 for example includes a pair of knobs 60 and 62 screwable to each other, for example through a threaded shaft extending from one of the knobs 60 or 62 screwable in a threaded aperture of the other knob 62 or 60. When the knobs 60 and 62 are fully tightened, the arm pivot 54 is prevented from translating along the arm slots 56 through friction and the threaded shaft 64 maintains the first, second, third and fourth arms 22, 24, 26 and 28 fixed relative to the arm pivot 58 in a direction perpendicular to the arm slots 56, achieving a locked configuration. When the knobs 60 and 62 are loosened, translations of the arm pivot 58 relative to the arm slots 56 is allowed, forming a free moving configuration. In some embodiments, the tightness of the arm pivot 58 may be selected such that translations of the arm pivot 58 along the arm slots 56 is prevented, but rotations of first, second, third and fourth arms 22, 24, 26 and 28 relative to each other is allowed, forming a rotatable configuration.

The holder assembly 20 is configured to hold the catheter device 12. In a specific embodiment of the invention, the holder assembly 20 is configured to hold a catheter device 12 including first and second components 14 and 16, including respective first and second catheters 66 and 68. The first component is for example for supporting a sheath through which other catheters are to be inserted. The second catheter 68 is designed to be inserted in the first catheter 66. The first and second components 14 and 16 are mountable respectively to first and second holder elements 70 and 72, or platforms, each mountable to a holder base 74 all part of the holder assembly 20. The configurations of the first and second holder elements 70 and 72 depends on the function and shape of the first and second components 14 and 16. The first and second holder elements 70 and 72 may be removable from the remainder of the holder assembly 20 to customize the latter for different catheter device 12 by using first and second holder elements 70 and 72 shaped to receive each specific catheter device 12 that is usable with the catheter device support stand.

In a specific embodiment, the first holder element 70 is slidably mountable on a mounting shaft 76 part of the holder base 74 and securable thereto using a set screw (not shown in the drawings) or in any other suitable manner. The first holder element 70 defines a groove 78 for receiving a suitably shaped portion of the first component 14. A bolt 80 is usable to selectively secure the first component 14 in the groove 78. In some embodiments, the first component 14 includes a cylindrical mounting portion 82 coaxial with the first catheter 66 and insertable in the groove 78, which allows to selectively rotate the first component 14 relative to the groove 78 when the bolt 80 is loosened. In addition, the cylindrical mounting portion 82 may be translated relative to the groove 78 when the bold 80 is loosened.

The second holder element 72 is, for example, dovetailed in an elongated mounting slot 84 formed in the holder base 74 so as to be movable longitudinally along the mounting slot 84. Any other suitable manner of mounting the second holder element 72 to the holder base is also usable. Another bolt 80 screwable in the second holder element 72 may be used to lock the second holder element 72 relative to the mounting slot 84 through frictional engagement with the holder base 74. The second component 16 defines a pair of second component circumferential grooves 86 and 88 and the second holder element 72 includes a pair of C-shaped supports 90 and 92 opening upwardly and each receivable in a respective one the second component grooves 86 and 88 to mount the second component 14 to the second holder element 72. In some embodiments, the second component 14 may be axially rotated relative to the C-shaped supports 90 and 92 with the second component circumferential grooves 86 and 88 remaining mounted thereto. Friction between the C-shaped supports 90 and 92 and the second component 14 maintain their relative orientation fixed when the latter is not actively rotated.

Figure 4B:
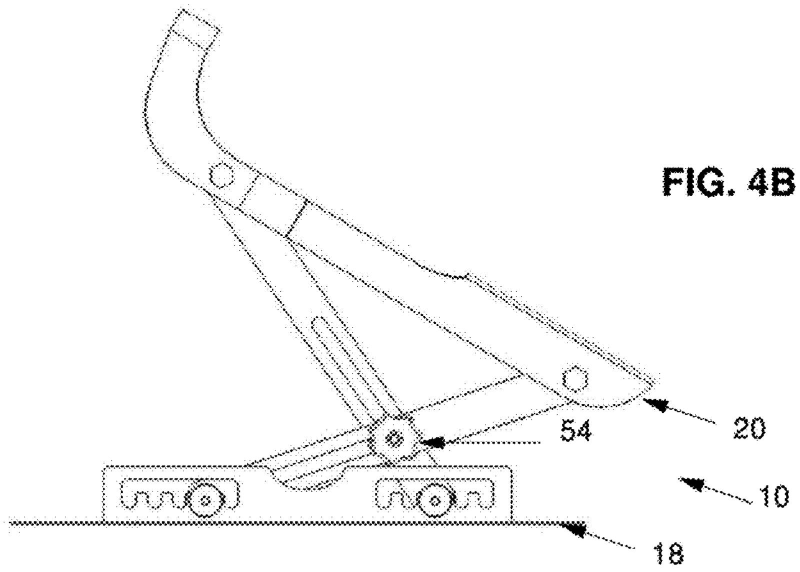
FIG. 4B, in a side elevation view, illustrates the catheter device support stand shown in FIG. 1 with the holder assembly rotated in a first direction relative to in the level position.
Figure 4C:
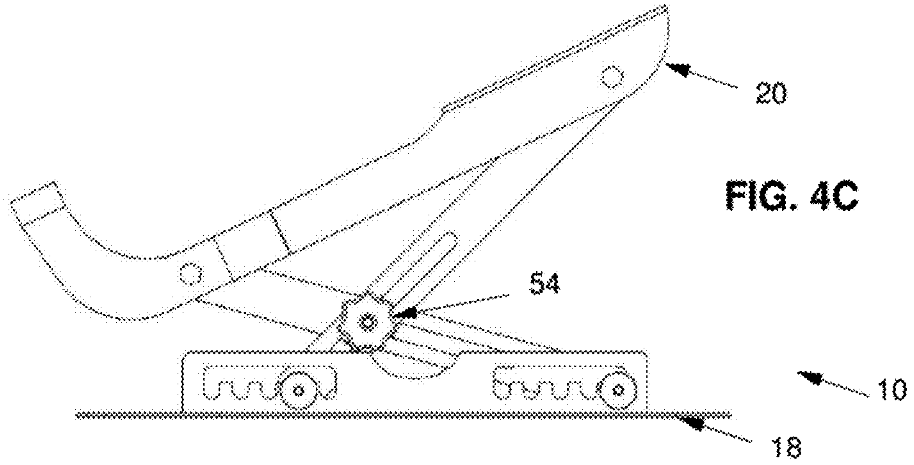
FIG. 4C, in a side elevation view, illustrates the catheter device support stand shown in FIG. 1 with the holder assembly rotated in a second direction opposite the first direction relative to in the level position.

In use, one may adjust the height of the holder assembly 20 relative to the base 18 by moving the base pivots 42 along the base slots 44, as seen in FIGS. 3A and 3B. If the base pivots 42 are moved relative to each other as a mirror image of each other relative to a longitudinal midpoint between the base slots 44, only the height of the holder assembly 20 is affected, and not its orientation relative to the base 18. This orientation can be changed by loosening the arm pivot 54 and manually tilting the holder assembly 20, as seen in FIGS. 4A to 4C, followed by tightening the arm pivot 54 once a desired orientation has been reached. By inserting the base pivots 42 in the notches 46, one can vary the height of the holder assembly 20 over the base 18 in discrete steps. In some embodiments, this height adjustment is performed first, followed by angle adjustment.

Figure 5A:
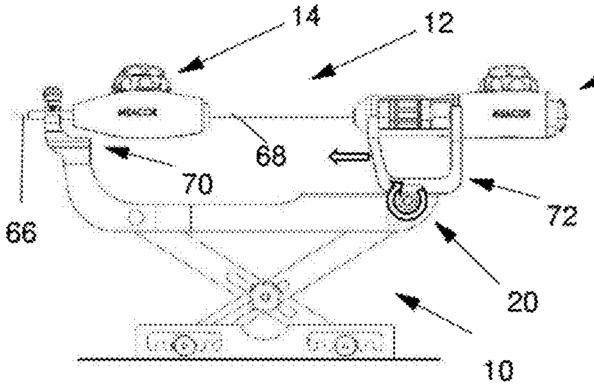
FIG. 5A, in a side elevation view, illustrates the catheter device support stand shown in FIG. 1 with the holder assembly with a holder element thereof in a rearmost position.
Figure 5B:
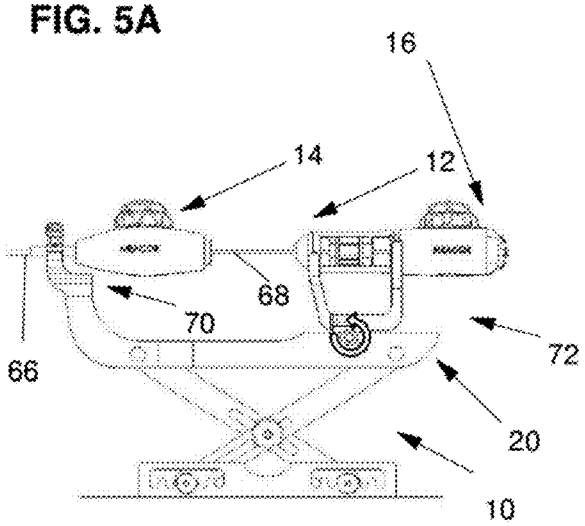
FIG. 5B, in a side elevation view, illustrates the catheter device support stand shown in FIG. 1 with the holder element in a frontmost position.

Additional degrees of freedom are provided in the holder assembly 20. As mentioned above, the second component 14 can be moved along the holder assembly 20 by moving the second holder element 72 along the holder assembly, as seen in FIGS. 5A and 5B. This allows one to vary a distance between the first and second components 14 and 16 so that the second catheter 68 is inserted to a varying degree in the first catheter 66. If the range of motion of the second holder element 72 is large enough, one may insert the second catheter 68 in the first catheter 66 after the latter has been inserted in a patient or replace the second component 16 with an alternative one during the course of a surgery.

Figure 6A:
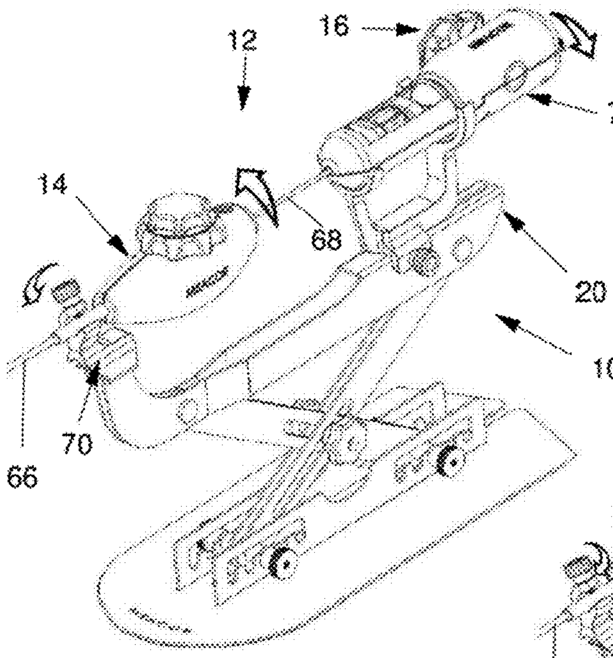
FIG. 6A, in a side elevation view, illustrates the catheter device support stand shown in FIG. 1 with first and second components of the catheter device mounted thereto in a first axial orientation relative to the holder assembly.
Figure 6B:
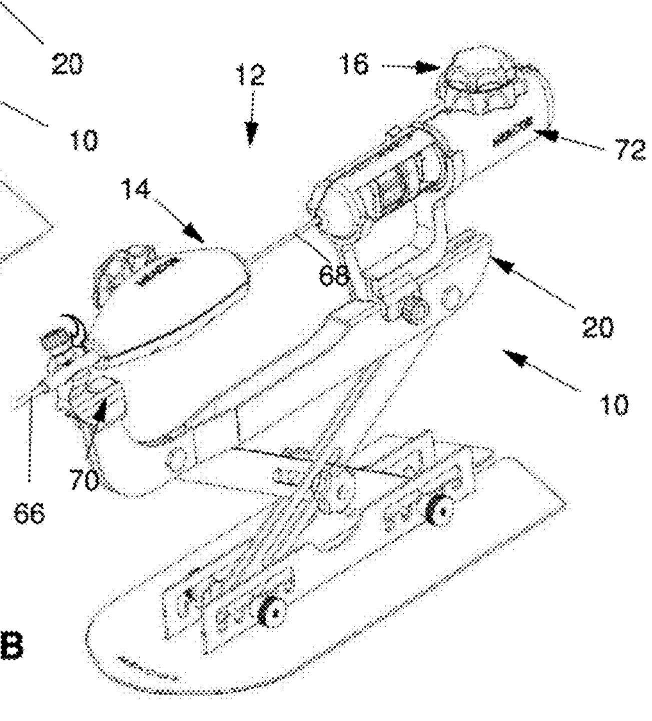
FIG. 6B, in a side elevation view, illustrates the catheter device support stand shown in FIG. 1 with the first and second components in a second axial orientation relative to the holder assembly differing from the first axial orientation.

Furthermore, the first and second components 14 and 16 are rotatable axially independently from each other about an axis passing through respectively the first and second catheters 66 and 68, which is also useful in many interventions, for example to rotate one of the first and second catheters 66 or 68 relative to the other, for example to better position an inner one of the first and second catheters 66 or 68 relative to the other. This is illustrated in FIGS. 6A and 6B.

Figure 7:
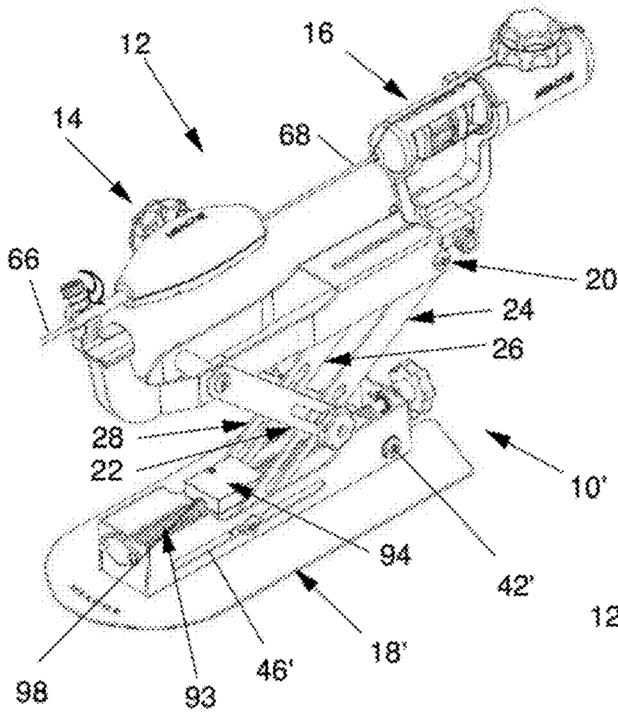
FIG. 7, in a perspective view, illustrates a catheter device support stand in accordance with an alternative embodiment of the present invention.
Figure 8:
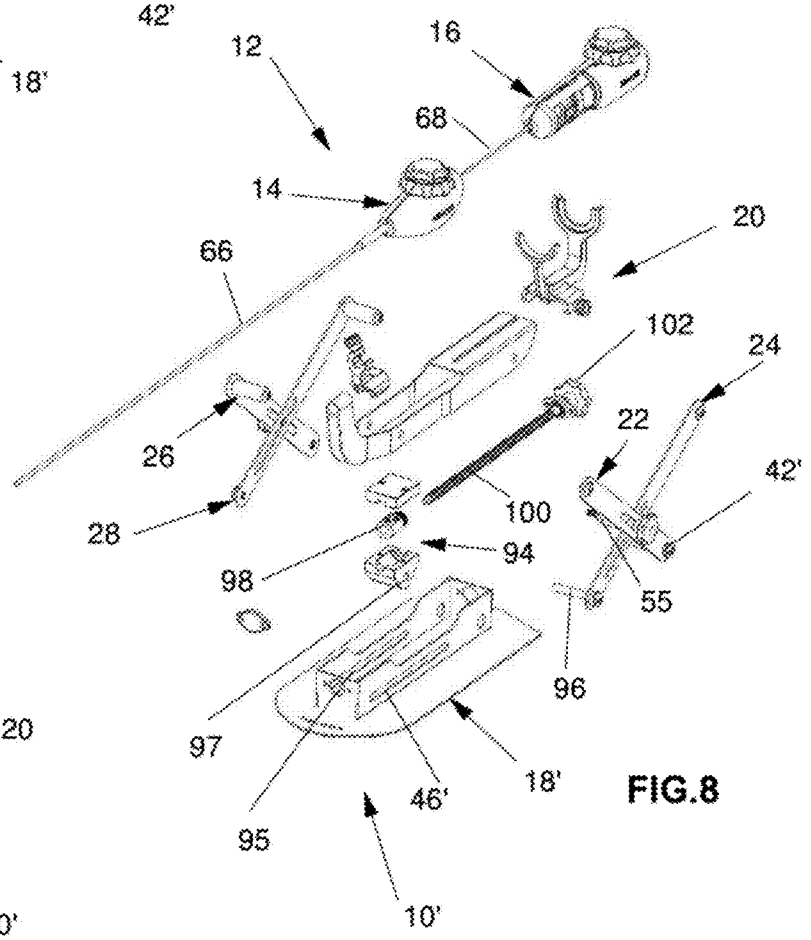
FIG. 8, in a perspective exploded view, illustrates the catheter device support stand shown in FIG. 7.

FIGS. 7 and 8 illustrates an alternative catheter device support stand 10' that is similar in many respects to the catheter device support stand 10. Only the differences between the two catheter device support stands 10 and 10' are described herein. One difference between the two catheter device support stands 10 and 10' resides in the manner in which the first, second, third and fourth arms 22, 24, 26 and 28 are mounted to an alternative base 18'. Indeed, in the catheter device support stand 10, only one pair of arms, either the first and third arms 22 and 26, or as seen in FIGS. 7 and 8, the second and fourth arms 24 and 28, is coupled to the base 18' so as to be movable therealong. The two other arms, the first and third arms 22 and 26 in the drawings, are pivotally secured to the base 18' through a fixed arm pivot 42'.

Figure 9:
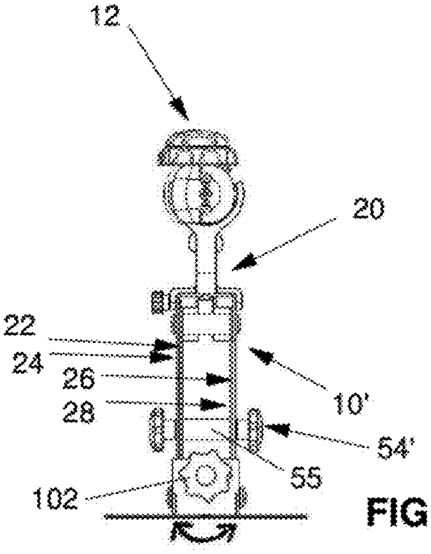
FIG. 9, in a rear end view, illustrates the catheter device support stand shown in FIG. 7.

The second and fourth arms 24 and 28, that are movable along the base 18', are pivotally secured to a carriage 94 which is slidable along the base 18' using a lead screw mechanism 93. The carriage 94 is configured to engage the base 18' so as to be fixed in rotation relative thereto. For example, the base 18' defines an elongated groove 95 in which the carriage 94 is slidable, the carriage 94 being relatively tightly received in the groove 95. A pin 96 extends through the second and fourth arms 24 and 28 adjacent the base 18' and through a pin receiving through aperture of the carriage 94. The pin 96 also extend through a pair of laterally spaced apart base slots 46', which are typically not notched. The carriage 94 defined a threaded aperture 98 extending parallel to the groove 95 through which a lead screw 100 extends. The lead screw 100 is mounted to the base 18' and is provided with an end knob 102 jointly rotatable therewith positioned to allow an operator to rotate the end knob 102. The end knob 102 is otherwise fixed relative to the base 18, such that rotations of the end knob 102 result in movements of the carriage 94 along the base 18'. Since the carriage 94 is between the second and fourth arms 24 and 28, the pivot 54' includes a spacer 55 between the second and fourth arms 24 and 28, as seen in FIG. 9.

As seen in FIGS. 10A and 10B, such rotations of the end knob 102, which move the carriage 94 along the base 18', result in variations in height of the holder assembly 20 relative to the base 18'. The lead screw mechanism 93 is relatively easy to operate to adjust the height of the holder assembly 20 relatively precisely. As previously, loosening of the arm pivot 54 allows to vary the position of the arm pivot 54 along the first, second, third and fourth arms 22, 24, 26 and 28 to change the relative angle between the base 18' and the holder assembly 20.

Figure 11:
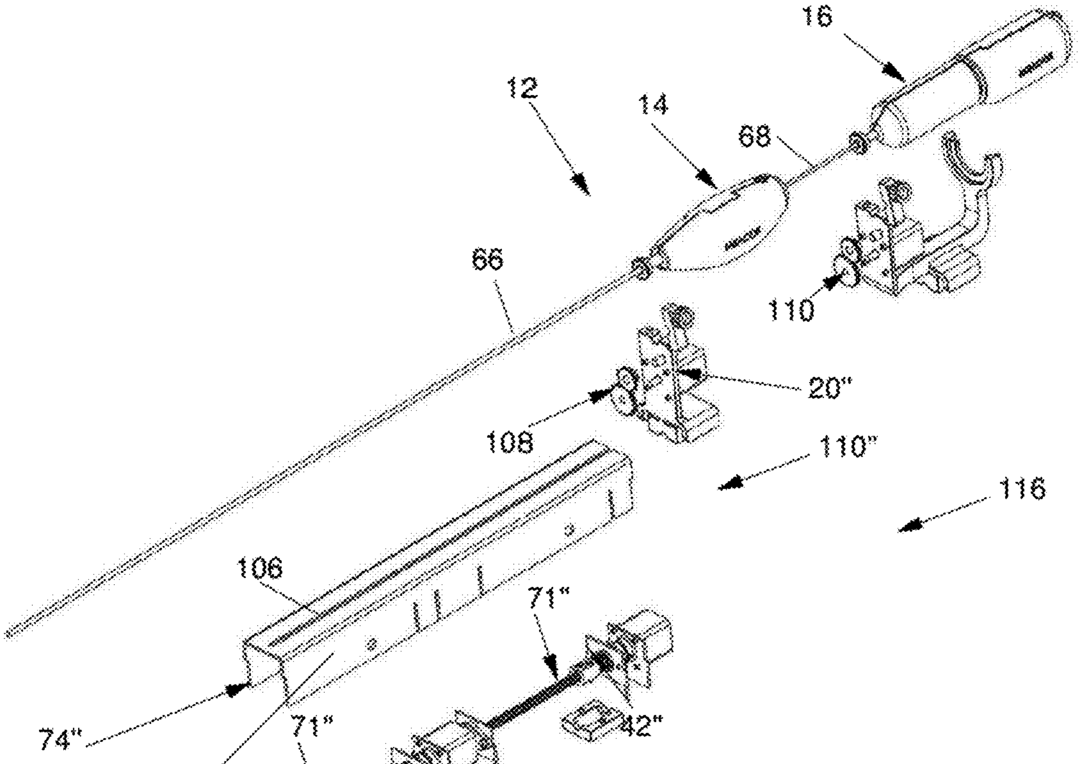
FIG. 11, in a perspective view, illustrates a catheter device support stand in accordance with another alternative embodiment of the present invention.
Figure 12:
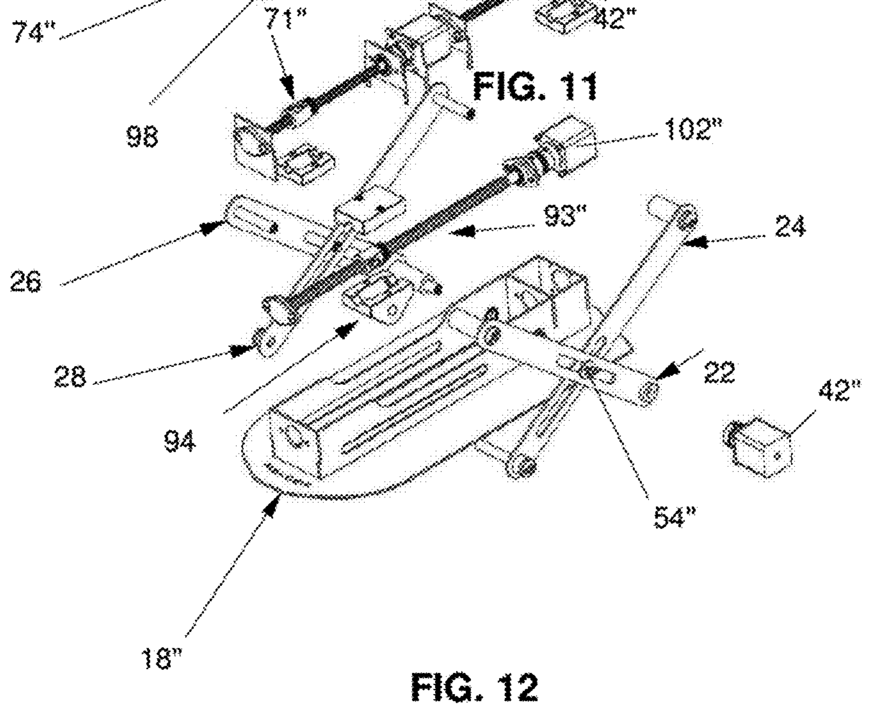
FIG. 12, in a perspective exploded view, illustrates the catheter device support stand shown in FIG. 11.
Figure 13A:
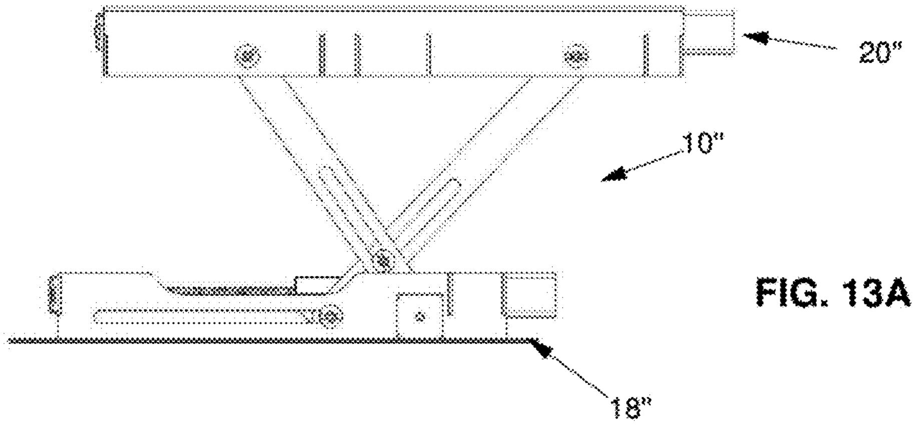
FIG. 13A, in a side elevation view, illustrates the catheter device support stand shown in FIG. 11 with a holder assembly thereof in an uppermost and level position.
Figure 13B:
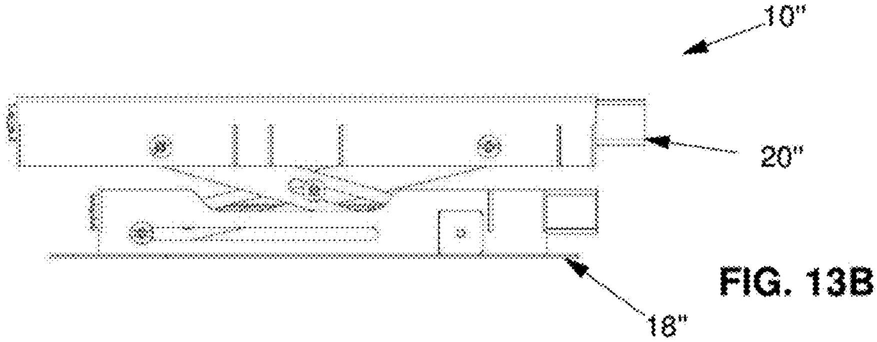
FIG. 13B, in a side elevation view, illustrates the catheter device support stand shown in FIG. 11 with the holder assembly in a lowermost and level position.
Figure 13C:
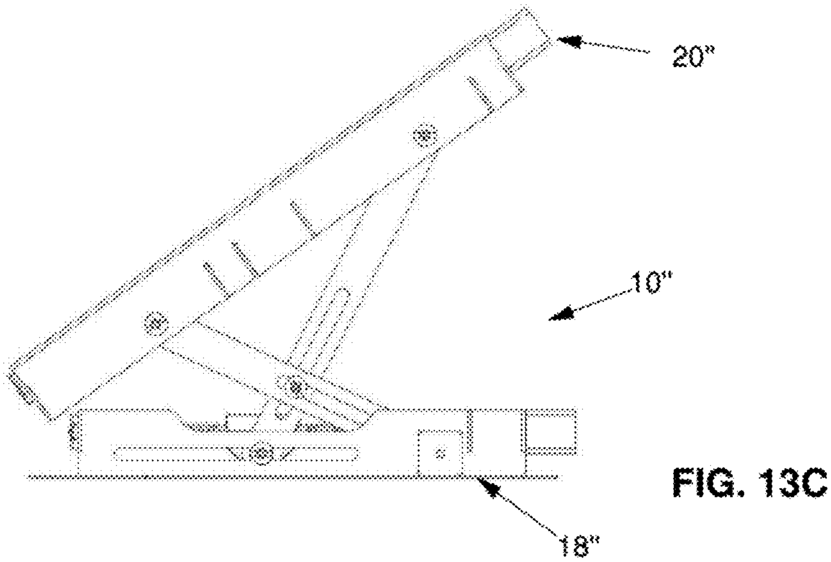
FIG. 13C, in a side elevation view, illustrates the catheter device support stand shown in FIG. 11 with the holder assembly a position intermediate the lowermost and uppermost positions with the holder assembly inclined relative to the level position.
Figure 14A:
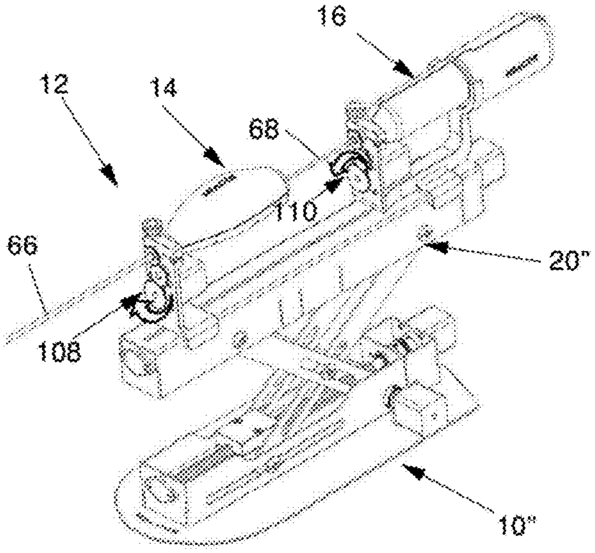
FIG. 14A, in a side elevation view, illustrates the catheter device support stand shown in FIG. 11 with first and second components of the catheter device mounted thereto in a first axial orientation relative to the holder assembly.
Figure 14B:
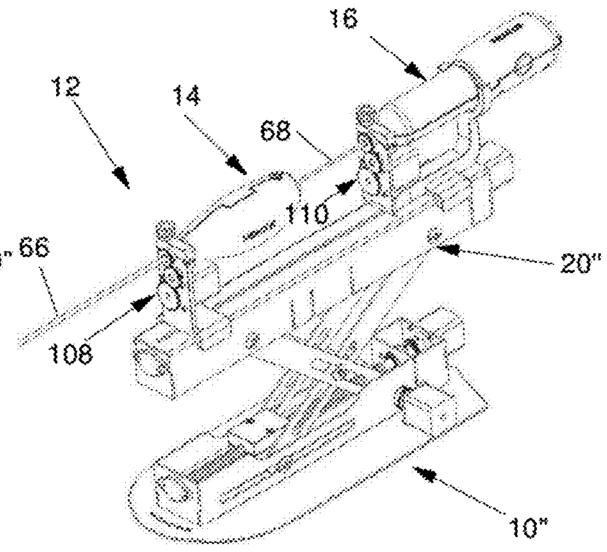
FIG. 14B, in a side elevation view, illustrates the catheter device support stand shown in FIG. 11 with the first and second components in a second axial orientation relative to the holder assembly differing from the first axial orientation.

FIGS. 11 and 12 illustrates yet another catheter device support stand 10" similar to the catheter device support stand 10'. As in the catheter device support stand 10', the catheter device support stand 10" includes a lead screw mechanism 93" at the base 18". However, instead of end knob 102, the lead screw 100 is rotated through a base motor 102", which is for example a step motor. Also, the arm pivot 54" is always in a loosened state, and an angle of two arms, for example the first and third arms 22 and 26 is controlled through an arm angle motor 42" actively pivoting the first and third arms 22 and 26 about the base 18", instead of having the base pivot 42. A similar arrangement with a knob replacing the motor 42" is usable in the catheter device support stand 10' to adjust the angle of the first and third arms 22 and 26. Friction provided by a lock or a gear mechanism may be used to hold constant this angle once adjustments have been made.

Figure 15:
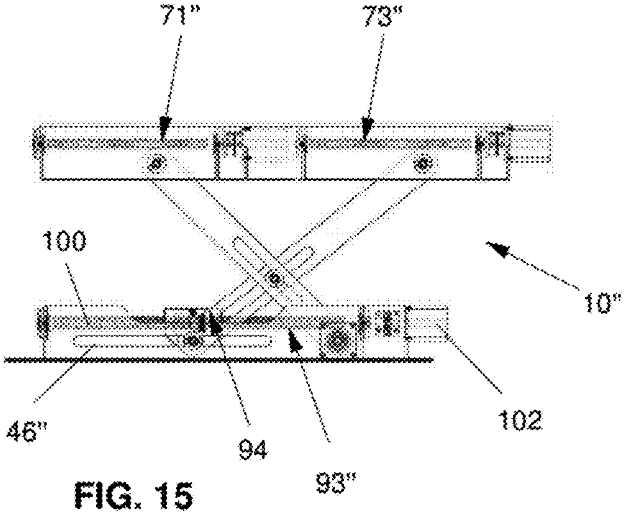
FIG. 15, in a side elevation view with hidden components shown, illustrates lead screw mechanisms part of the catheter device support stand shown in FIG. 11.

In some embodiments, the first and second holder elements 70" and 72" are also motorized. More specifically, the first and second holder elements 70" and 72" are each movable along the holder base 74" using a respective motorized lead screw mechanism 71" and 73" (seen for example in FIG. 15), each of which is similar to the lead screw mechanism 93", but with a shorter range of motion. Referring to FIG. 11, the first and second holder elements 70" and 72" are coupled to the lead screw mechanism 71" and 73" through an elongated slit 106 extending through an upper wall of the holder base 74". In some embodiments, the range of motion along which the second holder element 72" is movable is similar to the length of the second catheter 68, which may be advantageous in robotic catheter insertion.

In addition, the first and second holder elements 70" and 72" also include respectively first and second axial rotation mechanisms 108 and 110 that allow to selectively rotate axially the first and second catheters 66 and 68 independently from each other, for example by rotating the entire first and second components 14 and 16 about the first and second catheters 66 and 68. The first and second axial rotation mechanisms 108 and 110 are similar to each other and only the first axial rotation mechanism 108 is described in details below, with the understanding that the second axial rotation mechanism 110 is similar or identical thereto and operates in a similar manner.

Figure 16:
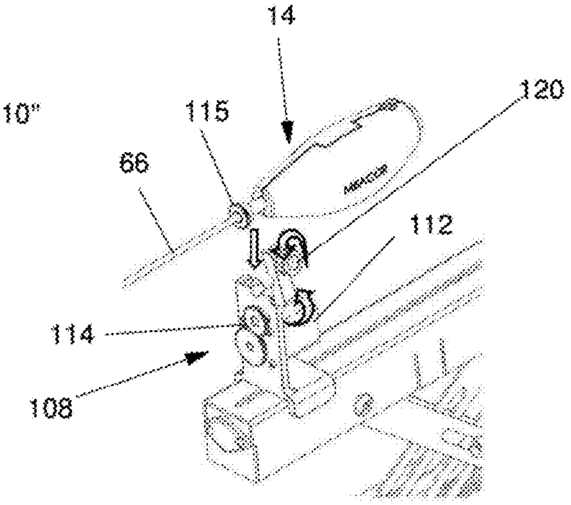
FIG. 16, in a perspective view, illustrates an axial rotation mechanisms part of the part of the catheter device support stand shown in FIG. 11.

Referring to FIG. 16, the first axial rotation mechanism 108 includes a motor 112 that engages a gear train 114. The gear train 114 is configured to engage a gear 115 when the first component 14 is operatively mounted to the catheter device support stand 10". The gear 115 is provided in periphery of the first catheter 66 in the first component 14 and is jointly rotatable therewith. Rotating the motor 112 will cause selective rotation of the first component 14 about the central axis of the first catheter 66, which is useful in some catheter procedures. The first component 14 may be removably mounted to the first axial rotation mechanism 108 through a clamp 120 that may be selectively open, to allow insertion and removal of the first component 14, and closed, to maintain the first component 14 secured thereto with the gear train 114 engaging the gear 115. When the first component 14 is held by the clamp 120, the first component 14 is free to rotate axially about the gear 115. Such rotations may be achieved in any other suitable manner.

The lead screw mechanisms 93", 71" and 73", as well as the first and second axial rotation mechanisms 108 and 110 may all be connected to a controller 116 provided with a user interface 118 and usable by an intended user to selectively activate independently from each other the motors of these components to operate the catheter device support stand 10". For example, the user interface 118 includes push-buttons allowing the intended user to control rotation of the various motors contained in the catheter device support stand 10" in opposed directions.

In some embodiments, the catheter device support stand 10" may be controlled locally or remotely over a network using a dedicated controller or a computer system 200. An example of such a computer system 200 is shown in FIG. 17. The computer system 200 that is programmed or otherwise configured to operate the catheter device support stand 10" by selectively energizing the various motors contained in the catheter device support stand 10".

The computer system 200 includes a central processing unit (CPU, also "processor" and "computer processor" herein) 205, which can be a single core or multi core processor, or a plurality of processors for parallel processing. The computer system 200 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 200 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 200, can implement a peer-to-peer network, which may enable devices coupled to the computer system 200 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 200 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 200 in some cases can include one or more additional data storage units that are external to the computer system 200, such as located on a remote server that is in communication with the computer system 200 through an intranet or the Internet.

In some embodiments, the computer system 200 can communicate with one or more remote computer systems through the network 230. The computer system 200 is also operative for energizing the motors of the system 10". For example, the peripheral devices 225 include a dedicated interface 245 including the required control logic and power control components required to power these motors. This dedicated interface may be provided in a separate device connected to the remainder of the computer system 200 through an interface, for example and non-limitingly a USB bus. The dedicated interface 245 may also be integrated on a card inserted in a suitable slot of a motherboard, such as a PCI slot, non-limitingly. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can, in some embodiments, access the computer system 200 via the network 230.

Control of the catheter device support stand 10" is effected through executable code stored on an electronic storage location of the computer system 200, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code, or can be compiled during runtime. The code can be supplied in a programming language that can be selected to enable the code to execute in a pre-compiled or as-compiled fashion. The code may provide a user interface allowing commands to be entered, and a control module controlling the dedicated interface, for example in the form of a device driver.

Aspects of the computer system 200 can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 200 can include or be in communication with an electronic display 235 that comprises a user interface (UI) 240 for providing, for example, controls corresponding to the various movements that the catheter device support stand 10" can perform. In other embodiments, the user interface allows an intended user to specify a final physical configuration to be achieved in the device catheter device support stand 10", and the various motors may be controlled to achieve this configuration. Examples of UI's include, without limitation, a graphical user interface (GUI) and web-based user interface.

Although the present invention has been described hereinabove by way of exemplary embodiments thereof, it will be readily appreciated that many modifications are possible in the exemplary embodiments without materially departing from the novel teachings and advantages of this invention. Accordingly, the scope of the claims should not be limited by the exemplary embodiments, but should be given the broadest interpretation consistent with the description as a whole. The present invention as described can be modified without departing from the spirit and nature of the subject invention as defined in the appended claims.

What is claimed is:

1. A support stand for a minimally invasive surgical instrument, the support stand comprising:

first and second arms intersecting each other at an arm pivot; and an instrument holder for holding the minimally invasive surgical instrument, the instrument holder being supported by the first and second arms; wherein the first and second arms are selectively pivotable relative to each other about the arm pivot, and wherein the arm pivot is selectively movable along the first and second arms, wherein the arm pivot is configurable between a locked configuration, a rotatable configuration and a free moving configuration, wherein:

in the locked configuration, the first and second arms are pivotally fixed relative to each other and the pivot is fixed along the first and second arms;

in the rotatable configuration, the first and second arms are pivotable relative to each other and the pivot is fixed along the first and second arms; and in the free moving configuration, the first and second arms are pivotable relative to each other and the pivot is movable along the first and second arms.

2. The support stand of claim 1, further comprising a base, the first and second arms extending between the instrument holder and the base, wherein pivoting the first and second arms relative to each other and moving the arm pivot along the first and second arms allows varying a distance and a relative orientation between the base and the instrument holder.

3. The support stand in of claim 2, wherein each of the first and second arms defines an opposed arm base end and a holder end, respectively, at the base and at the instrument holder; and the arm base end of at least one of the first and second arms is selectively movable along the base.

4. The support stand of claim 3, wherein the first and second arms are pivotally mounted to the instrument holder at holder pivots fixed in translation along the instrument holder.

5. The support stand of claim 3, wherein the arm base end of both the first and second arms are selectively movable along the base.

6. The support stand of claim 5, wherein the base defines longitudinally spaced apart arm receiving portions for fixedly receiving the first and second arms at discrete longitudinal positions along the base.

7. The support stand of claim 6, wherein the arm receiving portions include spaced apart generally downwardly extending notches in which the base pivots are selectively insertable.

8. The support stand of claim 6, further comprising third and fourth arms respectively substantially parallel to and in register with the first and second arms.

9. The support stand of claim 3, further comprising a translation actuator for selectively moving the arm base end of the at least one of the first and second arms along the base.

10. The support stand of claim 9, wherein the translation actuator includes a lead screw extending along the base and a carriage movable along the lead screw through rotation of the lead screw, the at least one of the first and second arms being mounted to the carriage and pivotable relative thereto.

11. The support stand of claim 3, wherein an other one of the first and second arms different from the at least one of the first and second arms is fixed along the base and pivotally mounted thereto.

12. The support stand of claim 11, further comprising a rotation actuator for selectively pivoting the other one of the first and second arms about the base.

13. The support stand of claim 12, wherein the first and second arms are freely pivotable about the arm pivot and the arm pivot is freely movable along predetermined portions of the first and second arms.

14. The support stand of claim 13, wherein the first and second arms each define a longitudinally extending slot, the arm pivot being received in and guided by the slots.

15. The support stand of claim 1, wherein the arm pivot includes a knob selectively turnable to vary frictional forces between the first and second arms to move the arm pivot between the locked, rotatable and free moving configurations.

16. The support stand of claim 1, wherein the minimally invasive surgical instrument includes first and second components, the instrument holder being configured for supporting the first and second components so that a distance between the first and second components is selectively adjustable.

17. The support stand of claim 16, wherein the surgical instrument holder includes a holder base and a platform for supporting one of the first and second components, the platform being longitudinally movable along the holder base.

18. The support stand of claim 17, further comprising a platform actuator for selectively moving the platform along the holder base.

19. The support stand of claim 1, wherein the surgical instrument includes a catheter, the instrument holder holding the surgical instrument so that the surgical instrument is selectively rotatable about a rotation axis colinear with the catheter.

20. The support stand of claim 19, further comprising a rotation actuator for selectively rotating the surgical instrument about the rotation axis.

21. The support stand of claim 1, further comprising a controller for selectively energizing an actuator.

22. The support stand of claim 1, further including a lead screw mechanism acting on the first and second arms through rotation and including a lead screw, the at least one of the first and second arms being mounted to the lead screw mechanism and pivotable relative to each other upon the rotation of the lead screw.

23. The support stand of claim 22, wherein the lead screw mechanism includes a translation actuator for selectively moving the lead screw.

24. The support stand of claim 23, wherein the translation actuator is an end knob positioned to allow an operator to rotate the end knob.

25. The support stand of claim 23, wherein the translation actuator is an electric motor connected to a controller.

26. The support stand of claim 22, wherein the lead screw mechanism is located above a pivot point of the first and second arms.

27. A support stand for a minimally invasive surgical instrument, the support stand comprising:

first and second arms intersecting each other at an arm pivot; and an instrument holder for holding the minimally invasive surgical instrument, the instrument holder being supported by the first and second arms; wherein the first and second arms are selectively pivotable relative to each other about the arm pivot, and wherein the arm pivot is selectively movable along the first and second arms, wherein the arm pivot is configurable between a locked configuration, a rotatable configuration and a free moving configuration, wherein:

in the locked configuration, the first and second arms are pivotally fixed relative to each other and the pivot is fixed along the first and second arms;

in the rotatable configuration, the first and second arms are pivotable relative to each other and the pivot is fixed along one of the first and second arms; and in the free moving configuration, the first and second arms are pivotable relative to each other and the pivot is movable along the first and second arms.

28. The support stand of claim 27, wherein, in the rotatable configuration, the first and second arms are pivotable relative to each other and the pivot is fixed along the first and second arms.

29. The support stand of claim 27, further comprising a base, the first and second arms extending between the instrument holder and the base, wherein pivoting the first and second arms relative to each other and moving the arm pivot along the first and second arms allows varying a distance and a relative orientation between the base and the instrument holder.

30. The support stand in of claim 29, wherein each of the first and second arms defines an opposed arm base end and a holder end, respectively, at the base and at the instrument holder; and the arm base end of at least one of the first and second arms is selectively movable along the base.

31. The support stand of claim 30, wherein the first and second arms are pivotally mounted to the instrument holder at holder pivots fixed in translation along the instrument holder.

32. The support stand of claim 30, wherein the arm base end of both the first and second arms are selectively movable along the base.

33. The support stand of claim 32, wherein the base defines longitudinally spaced apart arm receiving portions for fixedly receiving the first and second arms at discrete longitudinal positions along the base.

34. The support stand of claim 32, wherein the arm receiving portions include spaced apart generally downwardly extending notches in which the base pivots are selectively insertable.

35. The support stand of claim 32, further comprising third and fourth arms respectively substantially parallel to and in register with the first and second arms.

36. The support stand of claim 30, further comprising a translation actuator for selectively moving the arm base end of the at least one of the first and second arms along the base.

37. The support stand of claim 36, wherein the translation actuator includes a lead screw extending along the base and a carriage movable along the lead screw through rotation of the lead screw, the at least one of the first and second arms being mounted to the carriage and pivotable relative thereto.

38. The support stand of claim 30, wherein an other one of the first and second arms different from the at least one of the first and second arms is fixed along the base and pivotally mounted thereto.

39. The support stand of claim 38, further comprising a rotation actuator for selectively pivoting the other one of the first and second arms about the base.

40. The support stand of claim 39, wherein the first and second arms are freely pivotable about the arm pivot and the arm pivot is freely movable along predetermined portions of the first and second arms.

41. The support stand of claim 40, wherein the first and second arms each define a longitudinally extending slot, the arm pivot being received in and guided by the slots.

42. The support stand of claim 27, wherein the arm pivot includes a knob selectively turnable to vary frictional forces between the first and second arms to move the arm pivot between the locked, rotatable and free moving configurations.

43. The support stand of claim 27, wherein the minimally invasive surgical instrument includes first and second components, the instrument holder being configured for supporting the first and second components so that a distance between the first and second components is selectively adjustable.

44. The support stand of claim 43, wherein the surgical instrument holder includes a holder base and a platform for supporting one of the first and second components, the platform being longitudinally movable along the holder base.

45. The support stand of claim 44, further comprising a platform actuator for selectively moving the platform along the holder base.

46. The support stand of claim 27, wherein the surgical instrument includes a catheter, the instrument holder holding the surgical instrument so that the surgical instrument is selectively rotatable about a rotation axis colinear with the catheter.

47. The support stand of claim 46, further comprising a rotation actuator for selectively rotating the surgical instrument about the rotation axis.

48. The support stand of claim 27, further comprising a controller for selectively energizing an actuator.

49. The support stand of claim 27, further including a lead screw mechanism acting on the first and second arms through rotation and including a lead screw, the at least one of the first and second arms being mounted to the lead screw mechanism and pivotable relative to each other upon the rotation of the lead screw.

50. The support stand of claim 49, wherein the lead screw mechanism includes a translation actuator for selectively moving the lead screw.

51. The support stand of claim 50, wherein the translation actuator is an end knob positioned to allow an operator to rotate the end knob.

52. The support stand of claim 50, wherein the translation actuator is an electric motor connected to a controller.

53. The support stand of claim 49, wherein the lead screw mechanism is located above a pivot point of the first and second arms.

* * * * *